United States Patent [19]

Breuer et al.

[11] Patent Number: 5,196,409
[45] Date of Patent: Mar. 23, 1993

[54] BISPHOSPHONATES, PHARMACEUTICAL COMPOSITIONS, AND PROCESS FOR THE TREATMENT OF IRREGULARITIES IN CALCIUM METABOLISM

[75] Inventors: Eli Breuer, Jerusalem; Gershon Golomb, Efrat, both of Israel

[73] Assignee: Yissum, Research Development Company of the Hebrew University of Jerusalem, Jerusalem, Israel

[21] Appl. No.: 764,035

[22] Filed: Sep. 23, 1991

Related U.S. Application Data

[62] Division of Ser. No. 570,266, Aug. 20, 1990, abandoned.

[30] Foreign Application Priority Data

Aug. 20, 1989 [IL] Israel ......................................... 91362

[51] Int. Cl.$^5$ ....................... A61K 31/66; C07F 9/40; C07F 9/38
[52] U.S. Cl. ................................... 514/108; 558/158; 558/161; 562/20
[58] Field of Search ............... 514/108; 558/158, 161; 562/20

[56] References Cited

U.S. PATENT DOCUMENTS 3,012,054 12/1961 Moss et al. ..................... 558/160

Primary Examiner—Mary C. Lee
Assistant Examiner—Michael G. Ambrose
Attorney, Agent, or Firm—Lowe, Price, LeBlanc & Becker

[57] ABSTRACT

Novel bisphosphonates comprise compounds of the formula (I)

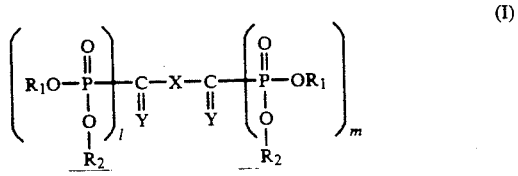

wherein m and l are independently 1 or 2; $R_1$ represents hydrogen, a lower alkyl group, or an alkali metal cation; $R_2$ represents hydrogen, a lower alkyl group or an alkali metal cation; Y represents =O or =N—OH, or —OH; and X represents —$(CH_2)_n$—, a branched alkylene group, or a branched or straight alkenylene or alkynylene chain optionally substituted by one or more oxygen or nitrogen atoms, wherein n is an integer from 3 to 24; with the provision that when l=m=1, Y is =O, and $R_1$ and $R_2$ denote a lower alkyl group, n represents an integer from 9 to 20; and with the provision that when l=m=2, Y is —OH and $R_1$ and $R_2$ are methyl groups, n represents an integer from 9-24; and with the further provision that when l=m=2, Y is —OH and $R_1$ and $R_2$ are hydrogen, n represents 3, 5 or an integer from 7 to 24; or X is —$(CH_2)_p$—$(OCH_2CH_2)_q$—O—$(CH_2)_{p'}$— wherein p and p' are independently integers from 1 to 5 and q is an integer from 1 to 6; or X is —$(CH_2)_t$—O—$(CH_2)_s$—O—$(CH_2)_{t'}$— wherein t and t' are independently integers from 1 to 6 and s is an integer from 2 to 12; or X is

—B—A—B wherein B represents a branched group or straight alkylene, or an alkenylene or alkynylene chain optionally substituted by one or more oxygen or nitrogen atoms, and A represents an aromatic group such as phenylene, naphthalenediyl, thiophenediyl or furandiyl.

20 Claims, 3 Drawing Sheets

FOREIGN PATENT DOCUMENTS 1010965 12/1957 Fed. Rep. of Germany ........ 562/20
1072346 12/1959 Fed. Rep. of Germany ........ 562/20

OTHER PUBLICATIONS

Rafik Karaman et al., Acylphosphonic Acids and Methyl Hydrogen Acylphosphonates: Physical and Chemical Properties and Theoretical Calculations, J. Chem. Soc. 1989.

Kanaan et al., Phosphorous and Sulfur, 1988, vol. 37, pp. 217–229.

Hilderbrand, CRC, "The Role of Phosphonates in Living Systems", pp. 55–96 1980.

Hilderbrand, CRC, "The Role of Phosphonates in Living Systems", pp. 161–188 1980.

BISPHOSPHONATES, PHARMACEUTICAL COMPOSITIONS, AND PROCESS FOR THE TREATMENT OF IRREGULARITIES IN CALCIUM METABOLISM

This application is a division of application Ser. No. 07/570,266 filed Aug. 20, 1990, now abandoned.

FIELD OF THE INVENTION

The present invention relates to novel bisphosphonates, processes for their preparation and pharmaceutical compositions containing the same. The compounds and the pharmaceutical compositions according to the present invention are suitable and useful for the treatment of irregularities in calcium metabolism.

BACKGROUND OF THE INVENTION

There are several pathological conditions that involve irregularities in calcium metabolism. Such are some bone related diseases as Paget's disease, osteoporosis as well as osteolysis in bone metastases.

Bone metastases present a major problem in many frequently occurring malignancies. Hypercalcemia, resulting from bone resorption, is a common and very important complication of malignancy, causing most distressful symptoms, such as severe pain, spontaneous fractures, and may lead to a metabolic coma and death. Moreover, neoplastic cell-induced osteolysis may determine the localization and growth enhancement of the tumor. (G. R. Mundy, Bone, 8, supp. 1, S9-5 16 (1987); Calcium in Biological Systems, R. P. Rubin, G. B. Weiss, and J. W. Putney, Jr. eds. Plenum Press, N.Y. (1985)). Ectopic calcification is a seemingly opposite type of pathological condition, characterized by the deposition for calcium phosphate in a number of clinically important diseases as, for example, atherosclerosis, kidney and renal calculus, arthritis, and bioprostetic heart valve calcification, and implanted biomaterial calcification such as bioprostetic and prosthetic heart valves, vascular grafts, LVAD (left ventricular assist devices), contact lenses and a total artificial heart.

Bisphosphonates are a relatively new class of drugs that have been developed for use in various metabolic diseases of bone, the target being excessive bone resorption and inappropriate calcification and ossification. (M. D. Francis and R. R. Martodam, in "The Role of Phosphonates in Living Systems" R. L. Hilderbrand, ed. CRC Press, Boca Raton, Fla, 1983, pp. 55-96; H. Fleisch, Bone, 1987, 8, Supp. 1, S23-S28). Recently there have been reports of encouraging clinical trials utilizing bisphosphonates to treat hypercalcemia in patients with breast cancer, myeloma, and bronchial carcinoma related osteolytic metastases, in addition to the established usage of bisphosphonates in Paget's disease and for diagnostic purposes in bone mapping. However, bisphosphonate therapy is frequently accompanied by severe side effects. Bisphosphonates have been also found highly potent both in inhibiting bioprosthetic heart valve calcification, and in experimental arteriosclerosis, however, this was accompanied by severe adverse effects on bone development and overall somatic growth.

The currently used bisphosphonates all belong to the geminal type, in which the two phosphoryl groups are bound to the same carbon ("P-C-P"), and therefore may be viewed as pyrophosphate analogs in which the oxygen between the two phosphorus atoms is replaced by a carbon.

In contrast, monophosphonates, vicinal bisphosphonates (P-C-C-P) and compounds in which the distance between the phosphoryl group is longer (P-$(C)_n$-P, n>2) are reported to be less active or inactive at all.

From the results obtained in various clinical studies using conventional bisphosphonates it appears that there is a need for compounds which have greater margin between the bone resorption inhibiting effect and that inhibiting mineralization, without an increase in toxicity.

According to the present invention it was found that introduction of modifications into long chain bisphosphonates of type P-$(C)_n$-P increases the cation binding ability of these compounds, and inhibits ectopic calcification. The advantage in this type of compound in interacting with calcium phosphate crystals is assumed to derive from the presence of an additional independent anchor site(s) in the molecule as compared with known bisphosphonates. An additional advantage of this novel class of compounds is an effect of long duration and the enhanced ability to interact with the cell membrane.

U.S. Pat.No. 3,012,054 from Mar. 18, 1960 and a paper by M. Kanaan and R. Burgada, Phosphorus and Sulfur, 1988, 37, 217-229, describe the preparation of "tetraalkyl esters of diphosphonates" having the structure:

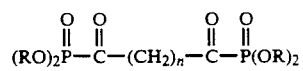

wherein R=alkyl radical containing 1-4 cabons and n=2 to 8, inclusive.

It should be emphasized that the patent mentioned deals only with tetraesters. It is well known that such dialkyl acylphosphonates, as mentioned, exhibit exteme instability toward water, and they hydrolyze to the corresponding carboxylic acids both in acidic and alkline conditions. Consequently, hydrolysis of the tetraalkyl esters desoribed in the patent and the paper cited above would lead to dicarboxylic acids HOOC—$(CH_2)_n$—COOH. Therefore, the syntheses of dealkylated derivatives such as represented by the formulas below:

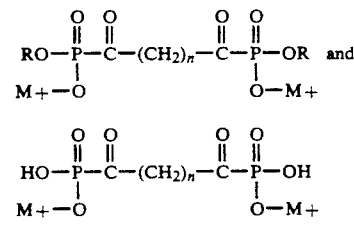

require special nonhydrolytic methods, and by no means are the dealkylated compounds obvious derivatives of the teraesters.

Neither esters nor acids of bisphosphonates in which the two ketophosphonic groups such as aromatic rings etc., have been reported.

SUMMARY OF THE INVENTION

The present invention relates to novel bisphosphonates of the formula (I)

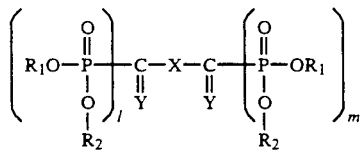 (I)

wherein m and l are independently 1 or 2; $R_1$ represents hydrogen, a lower alkyl group, or an alkali metal cation; $R_2$ represents hydrogen, a lower alkyl group or an alkali metal cation; Y represents =O or =N—OH, or —OH; and X represents —$(CH_2)_n$—, a branched alkylene group, or a branched or straight alkenylene or alkynylene chain optionally substituted by one or more oxygen or nitrogen atoms, wherein n is an integer from 3 to 24; with the provision that when l=m=1, Y is =O, and $R_1$ and $R_2$ denote a lower alkyl group, n represents an integer from 9 to 20; and with the provision that when l=m=2, Y is —OH and $R_1$ and $R_2$ are methyl groups, n represents an integer from 9-24; and with the further provision that when l=m=2, Y is —OH and $R_1$ and $R_2$ are hydrogen, n represents 3, 5 or an integer from 7 to 24; or X is

wherein p and p' are independently integers from 1 to 5 and q is an integer from 1 to 6; or X is

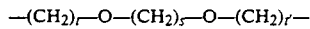

wherein t and t' are independently integers from 1 to 6 and s is an integer from 2 to 12; or X is

wherein represents a branched group or straight alkylene, or an alkenylene or alkynylene chain optionally substituted by one or more oxygen or nitrogen atoms, and A represents an aromatic group such as phenylene, naphthalenediyl, thiophenediyl or furandiyl.

Preferably $R_1$ is hydrogen or a methyl group, $R_2$ is a methyl group, or a sodium or lithium cation, Y is =O or =NOH, B is a —$CH_2$— group and A is phenylene, optionally substituted.

The present invention further relates to a process for obtaining the abovementioned compounds according to formula (I) and pharmaceutical compositions containing the same.

DETAILED DESCRIPTION

Figure 1:
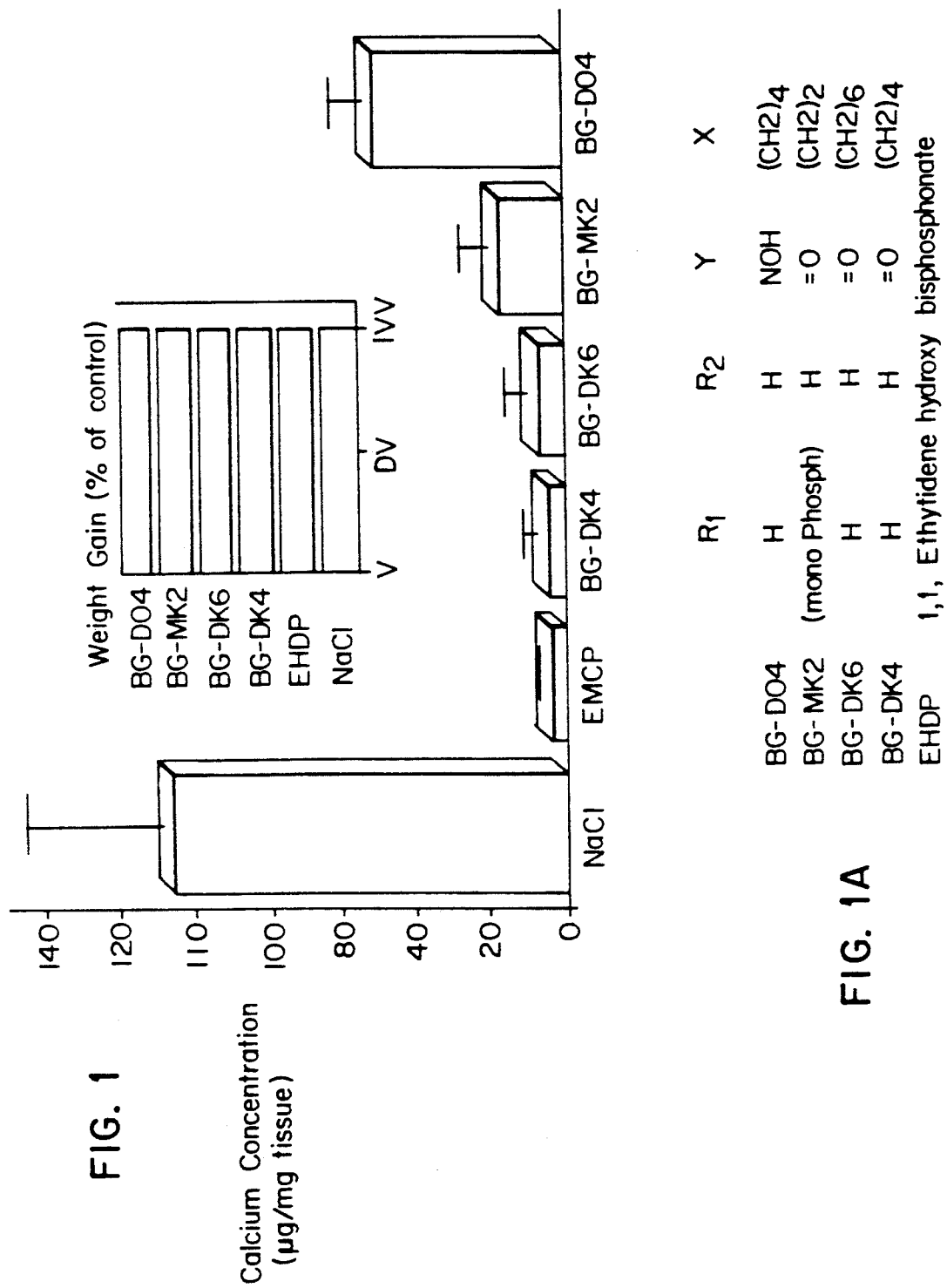

The process for the preparation of tetraalkyl $\alpha, \alpha'$-diketobisphosphonates comprises adding trimethyl phosphite to the corresponding dicarboxylic acid dihalide.

The process for obtaining dialkyl $\alpha\alpha'$-diketobisphosphonates disalts comprises adding tetraalkyl diketobisphosphonates dissolved in acetone or acetonitrile to a solution of sodium iodide or lithium bromide in acetonitrile.

The process for the preparation of hydrogen $\alpha,\alpha'$-diketobisphosphonate disalts (sodium) comprises dissolving tetraalkyl diketobisphosphonate in dry nonhydroxylic solvent and addition of bromotrimethylsilane.

The process for the synthesis of dialkyl $\alpha,\alpha'$-bishyroxyiminobisphosphonate disalts comprises suspending dimethyl dilithium $\alpha,\alpha'$-bishydroxyiminobisphosphonate, in absolute ethanol, and in a separate flask dissolving sodium in absolute ethanol. The resulting solution is added slowly to hydroxylamine hydrochloride in methanol.

The process for the synthesis of octa-alkyl $\alpha w'$ dihydroxy $\alpha\alpha$ ww tetrakisphosphonates is by adding $\alpha w$ diacyldihalide to a mixture of trialkyl phosphite and dialkyl phosphite.

The process for the synthesis of $\alpha w$ dihydroxy $\alpha\alpha$ ww tetrakisphosphonic acid consists of adding hydrochloric acid to the octaalkyl esters.

The present invention also relates to pharmaceutical compositions which comprise a compound according to the invention as active ingredient and suitable carriers optionally suitable for controlled release delivery systems and/or other additives.

The drug delivery systems may include any conventional suitable carrier or controlled release system (sustained release, delayed action preparations), based on a polymeric vehicle (e.g. silicon, polyurethane, or any other biocompatible polymer), or based on degradable systems (e.g. chitosan, collagen, or any other degradable/biodegradable carrier).

Chitosan is soluble only in acidic pH, preferably by acetic acid. Drug delivery systems based on chitosan as a carrier can be prepared in a conventional and in an innovative way. In the first method the drug is dissolved with the polymer in acidic pH (preferably, 1 to 10% w/w solids with acetic acid) and the solvent is evaporated or extracted by a non-solvent. By this method sustained release drug delivery systems in the form of film (matrix), micromatrics, microcapsules or microspheres could be prepared.

An innovative method of preparing chitosan-based drug delivery system is based on the alkalinity of chitosan (amino functional groups) and the acidity of phosphonates (as free acid obtained from the sodium salt by a catonic exchange resin). The drug in its acid form is reacted with chitosan yielding a soluble chitosan-phosphonate salt without the requirement for another exterior acid, followed by water evaporation/extraction as above. By this method the controlled release of the drug is governed not only by the matrix but also by the dissociation of the carrier-drug salt. Additional advantage is the possible targeting of the drug by chitosan. The chitosan-phosphonate salt could be embedded in chitosan for further delay of drug release.

The treatment with the controlled release delivery system is utilized by subdermal implantation (as was done in FIG. 1) or by site specific implantation, with the aim being optimization of therapy, using lower dosage, minimizing systemic side effects, and effective prolonged treatment with better patient compliance.

The novel bisphosphonates, according to the present invention, prevent calcium precipitation from metastable calcium and phosphate solution. Profound inhibition of rat, subdermal bioprosthetic heart valve tissue calcification was achieved, by coimplantion of Alzet osmotic pumps releasing the drug, and tissue cusps. Therapy was achieved without side effects, as exhibited by the normal somatic growth. These in-vivo results are summarized in FIG. 1.

The novel bisphosphonates, according to the present invention are useful in the treatment of the following diseases: Osteoporosis (including disuse and postmenopausal osteoporosis), Hypercalcemia of Malignancy, (Direct) anticancer effect, Heterotopic Ossification (Hip Arthroplasty, Spinal cord injury, Myositis ossificans), Paget's disease, Hyperphosphatemia (e.g. Diabetes).

It can be seen that said compounds are useful not only for direct treatment of various diseases but also for treatment of the symptoms of the diseases (e.g. Hyperphosphatemia or Hypercalcemia).

The compounds according to the present invention are also useful as diagnostics (e.g. Nuclear Medicine).

The compounds according to the present invention may possess also industrial applications which are listed below (R. L. Hilderbrand, The Role of Phosphonates in Living Systems, Chapter 7, page 172, CRC Press); Adhesives; Agents for extraction, concentration, and purification of uranium, thorium, and plutonium; Antioxidants; Antistatic agents; Blowing agents; Catalysts; Corrosion inhibitors; Coupling agents; Crystallization inhibitors; Dentifrice compositions; Deodorants; Detergent additives; Detergents for cleaning metal surfaces; Dye modifiers; Flame retardant polymers; Flame retardants for textiles; Fire retardants for synthetic fibers; Flotation agents; Fuel additives; Gelling agents; Hardening oil composites; Heat and light stabilizers; Hydraulic fluid additives; Ion exchange resins; Lubricants; Photography; Plasticizers; Polyester, polyethylene, and polycarbonate discoloration inhibitors; Polyurethane additives; Rayon additives; Resin and plastic additives; Scale inhibitors; Settling retardants; Sequestering agents; Solvent extraction; Suspending agents; Synthetic fiber preparation; Viscosity modifiers; Wood fireproofing agents.

The invention is further illustrated by means of the following non-limiting examples.

EXAMPLES

General method for the synthesis of tetraelkyl $\alpha,\alpha'$-diketobisphosphonates. Trimethyl phosphite (0.4 mole) was added dropwise to the dicarboxylic acid dichloride (0.2 mole) at 5° C. After the addition was completed, the reaction mixture was stirred for 1 hr at ambient temperature.

Tetramethyl adipoylbisphosphonate was obtained in a yield of 90%. IR (neat) 1697s, 1260s, 1030s cm$^{-1}$. NMR; (CDCl$_3$) $^1$H: $\delta$ 3.87 (12H, J = 10.64 Hz), 2.85 (4H, m), 1.65 (4H, m).

Tetramethyl suberoylbisphosphonate was obtained in a yield of 90%. IR spectrum (neat) 1696s, 1265s, 1034s cm$^{-1}$. NMR (CDCl$_3$); $^1$H: $\delta$ 3.87 (12H, d, J = 10 Hz), 2.82 4H, t, J = 7.2 Hz), 1.63 (4H, m), 1.32 (4H, m), $^{31}$P: $\delta$ = 0.88 (sept). These compounds decomposed upon attempted distillation, but they were sufficiently pure to be used for the next step in the synthesis without further purification.

Synthesis of Me$_2$O$_3$P—CO—(CH$_2$)$_{10}$—CO—PO$_3$Me$_2$

Tetramethyl dodecanedioldiphosphonate. 8.03 g (0.03 mol) of dodecanedicyl dichloride was added, drop by drop, with stirring to a solution of 7.82 g (0.0636 mol) trimethyl phosphite in dry toluene at −10 C. under a nitrogen atmosphere. The reaction mixture was stirred at room temperature for about 24 h. The toluene and the excess trimethyl phosphite were evaporated at reduced pressure to yield an oily product. In the $^{31}$P nmr spectrum the product showed a septet at the chemical shift of $\delta$ −4.4 ppm.

General method for the synthesis of dialkyl $\alpha,\alpha'$-diketobisphosphonate disalts. Tetraalkyl diketobisphosphonate (0.5 mole) was dissolved in 50 ml dry acetone or acetonitrile, and the solution was added to a solution of sodium iodide (1.1 mole) in dry acetone (30 ml) or lithium bromide in acetonitrile. The reaction mixture was stirred overnight at room temperature. The precipitate was filtered, washed with dry acetone or acetonitrile and dried. The yields are > 85%.

Dimethyl dilithium adipoylbisphosphonates, yield was 95%, m.p. > 250° C., IR (nujol): 1660s, 1210s, 1110s, 1020s cm$^{-1}$. NMR (D$_2$O) $^1$H: $\delta$ 3.6 (6H, d, J = 10.67 Hz), 2.85 (4H, m), 1.6 (4H, m).

Dimethyl dilithium suberoylbisphosphonate, yield 100%, m.p. > 250° C., IR (nujol): 1670s, 1216s, 1110s, 1040s cm$^{-1}$. NMR (D$_2$O) $^1$H $\delta$ 3.65 (6H, d, J = 10.56 Hz), 2.87 (4H, t, J = 7.2 Hz), 1.64 (4H, m) 1.36 (4H, m).

General method for the synthesis of dihydrogen $\alpha,\alpha'$-diketobisphosphonate disalts (sodium). 0.01 mole of tetramethyl diketobisphosphonate was dissolved in dry acetonitrile (20 ml). 0.066 mole (9 ml) of bromotrimethylsilane was added slowly and the reaction mixture was stirred at ambient temperature for three hours. The acetonitrile was evaporated in vacuum (keeping the temperature below 30° C.). A solution of sodium hydroxide (0.02 Mole) in methanol (25 ml) was added to the residue and the reaction mixture was stirred overnight at the ambient temperature. The white precipitate was filtered, washed with methanol (15 ml) and dried.

Disodium dihydrogen adipoylbisphosphonate, yield 90%, m.p. > 250° C., IR KBr 1675s, 1191s, 1055s cm$^{-1}$. NMR (D$_2$O) $^1$H: $\delta$ 2.88 (4H, m), 1.6 (4H, m). $^{31}$P: $\delta$ = −2.98, −3.44 s. Anal.: Calcd.: C, 22.64; H, 3.14. Found: C, 22.41; H, 3.2.

Disodium dihydrogen suberoylbisphosphonate, yield 90%, m.p. > 250°. IR (KBr) 1677s, 1214s, 1110s, 1075s cm$^{-1}$. NMR (D$_2$O) $^1$H: $\delta$ 2.8 (4H, t, J = 7.2 Hz), 1.58 (4H, m), 1.31 (4H, m), $^{31}$P: $\delta$ = −3.23, 3.7s. Anal.: Calcd. C, 27.75; H, 4.05, Found, C, 26.93; H, 3.92.

Disodium dihydrogen terephthaloylbisphosphonate, yield 90%, m.p. > 250° C., IR: 1641, 1682 cm$^{-1}$.

Disodium dihydrogen isophthaloylbisphosphonate, yield 90%, m.p. > 250° C., IR: 1641 cm$^{-1}$.

Synthesis of MHO$_3$P—CO—(CH$_2$)$_{10}$—CO—PO$_3$HM (M = Cation, e.g. Na$^+$, Li$^+$, etc.)

Dihydrogen disodium dodecanedioylphosphonate. Tetramethyl dodecanedioyldiphosphonate obtained in the previous step was dissolved in dry benzene (30 ml) and cooled to 0° C. 30.2 g (0.198 mole) of bromotrimethylsilane was added slowly to the solution and the reaction mixture was stirred at the ambient temperature for one hour. The reaction mixture was evaporated in vacuum (keeping the temperature below 30°) and a solition of sodium hydroxide 2.4 g (0.06 mol) in methanol (70 ml) was added with stirring to the residue and the reaction mixture was stirred for 2 hrs. at ambient temperature and the white precipitate was filtered, washed with methanol (15 ml) and dried. In the −P nmr spectrum the product showed a singlet at $\delta$ −0.2 ppm. $^1$H nmr spectrum $\delta$ 2.50 ppm (4H, t), 1.24 ppm (4H, m), 0.99 ppm (12H, broad singlet).

Synthesis of dialkyl $\alpha,\alpha'$-bishydroxyiminobisphosphonate disalts. 0.01 mole of dimethyl dilithium $\alpha,\alpha'$-bishydroxyiminobisphosphonate was suspended in absolute ethanol (10 ml), in flask A. In a separate flask 0.03 mol sodium was dissolved in absolute ethanol (10 ml), in an ice bath under a reflux condenser, equipped with a calcium chloride tube. The resulting solution was added slowly to a solution of 0.03 mol hydroxylamine hydrochloride in methanol (15 ml), until the solution was neutral to pH paper. After stirring for 5 minutes in an ice bath, sodium chloride was filtered, washed with ethanol and the filtrate was added to the solution of dimethyl dilithium salt in flask A. The reaction mixture was left to stir for 1-2 days at the ambient temperature, it was filtered, washed successively with acetonitrile and ether and dried in vacuo at room temperature.

Dimethyl dilithium 1,6-bishydroxyiminohexmethylene-1,6-bisphosphonate was obtained in a yield of 90%, m.p.>250° C., IR (KBr): 1650w,b, 1221s, 1085s, 1049s cm$^{-1}$. NMR (D$_2$O) $^1$H: δ 3.55 (6H, d, J=10.8 Hz), 2.5 (4H, m), 1.62 (4H, m).

Dimethyl dilithium 1,8-bishydroxyiminooctamethylene-1,8-bisphosphonate yield 90%, m.p.>250° C., IR (KBr): 1665w,b, 1227s, 1087s, 1050s, cm$^{-1}$. NMR (D$_2$O): $^1$H δ 3.56 (6H, d, J=10.89 Hz), 2.5 (4H, m), 1.6 (4H, m), 1.4 (4H, m).

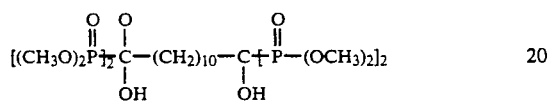

Octamethy 1,12-dihydroxydodecane-1,1,12,12-tetrakisphosphonate 5.34 g (0.02 mol) 1,12-dodecanedioyl dichloride was added dropwise, with stirring, in a nitrogen atmosphere, to a mixture of 4.96 g (0.04 mol) of trimethyl phosphite and 4.40 g (0.04 mol) of dimethyl phosphite at room temperature. The mixture was stirred for 10 hrs at 90° C. and the reaction mixture was evaporated under reduced pressure. The oily residue (9.8 g) showed a broad signal at δ=22.3 ppm in the $^{31}$P nmr spectrum.

1.12-Dihydroxydodecane-1,1,12,12-tetrakisphosphonic acid tetrasodium salt.

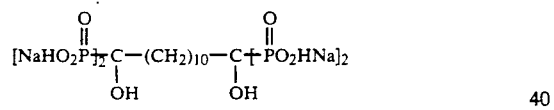

The product obtained in the previous step was dissolved in concentrated (32%) hydrochloric acid and refluxed for 72 hrs. The solution was cooled and filtered to remove impurities, the excess acid was evaporated, the residue dissolved in warm distilled water and concentrated solution of sodium hydroxide was added dropwise, to pH 4 when the product started to precipitate. The precipitate which was collected by filtration, showed in the $^{31}$p nmr spectrum a triplet at δ=19.58 ppm (J=14 Hz).

In vitro test:

A novel bisphosphonate according to the present invention was added to a mixture of calcium chloride and sodium phosphate. After a period of time the calcium and phosphous concentration in the filrate was determined.

Figure 2:
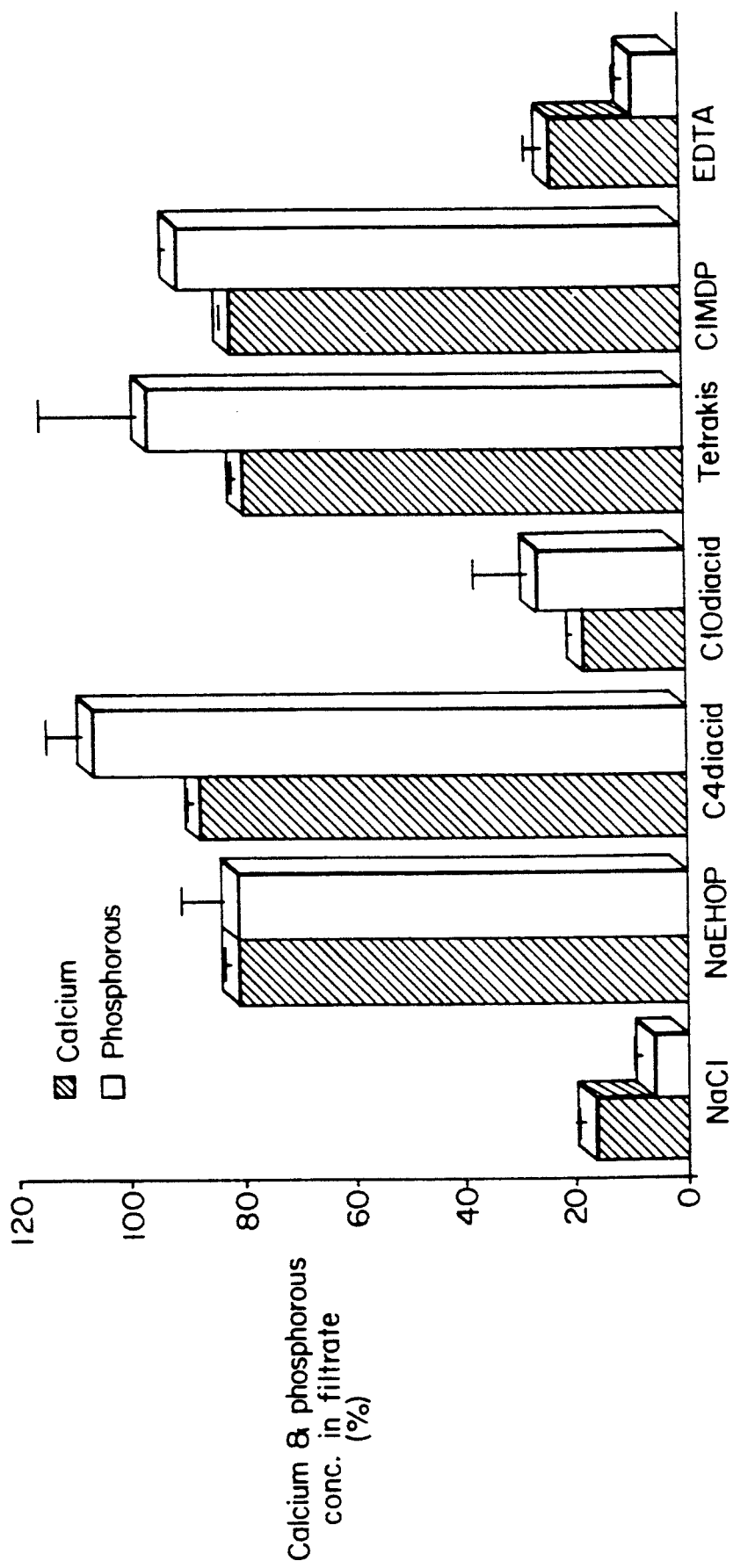

FIG. 2 shows that adipoylbisphosphonate (C4 diacid)

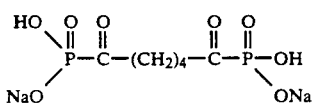

prevents the precipitation of calcium and phosphorus in the solution highly effectively while the C10 analog is only slightly effective.

The tetrakisphosphonate is also highly effective. The above novel phosphonates were compared to two commercial compounds

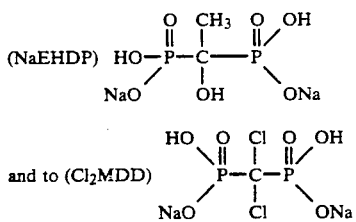

Figure 3:
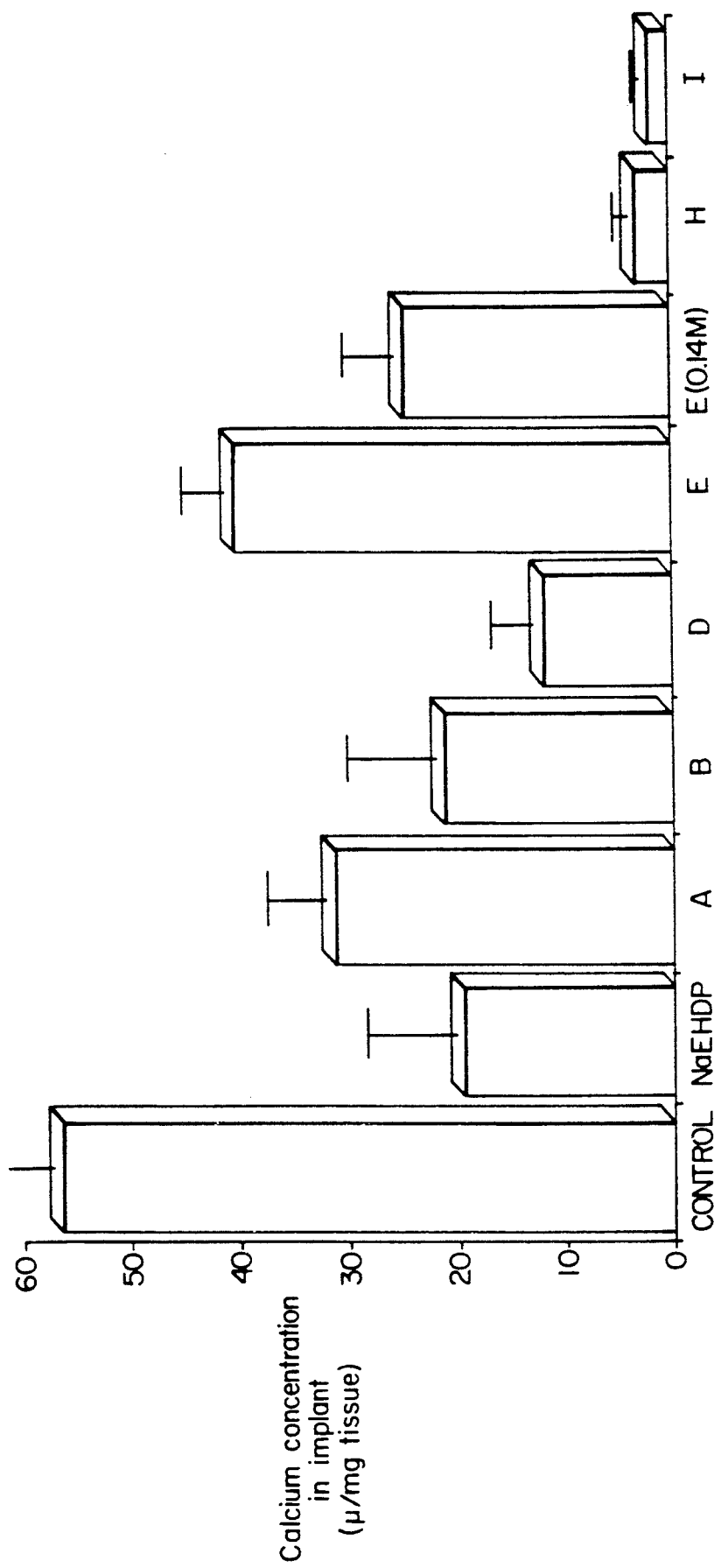

In vivo test:

FIG. 3 shows in vivo anticalcification effect of novel bisphosphonates.

The novel bisphosphonates were:

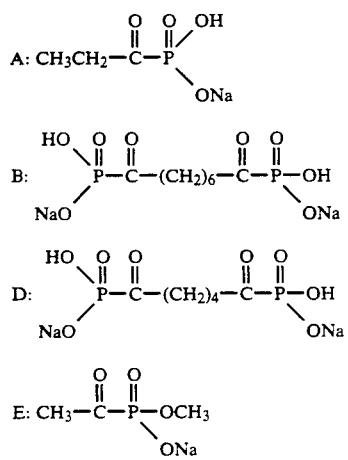

They were compared to the commercial compounds:

H: Cl$_2$MDP

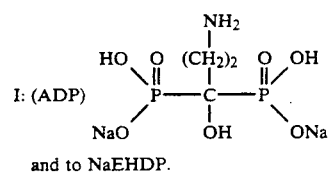

and to NaEHDP.

We claim:
1. Bisphosphonate compounds of the formula

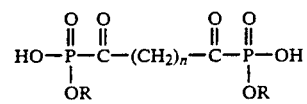

wherein
n=an integer from 3 to 24 and
R=hydrogen or a monovalent alkali metal cation.
2. A compound according to claim 1 having the formula

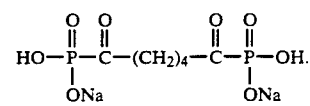

3. A compound according to claim 1 having the formula

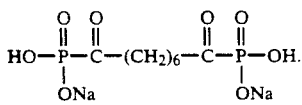

4. A compound according to claim 1 having the formula

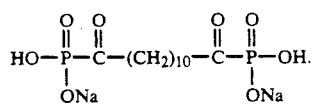

5. Pharmaceutical composition which comprises a compound according to claim 3 as an active ingredient, and a pharmaceutically acceptable carrier.

6. Pharmaceutical composition according to claim 5, wherein the carrier is suitable for a controlled release delivery system.

7. Pharmaceutical composition according to claim 6 wherein the carrier is based on a polymeric vehicle.

8. Pharmaceutical composition according to claim 7, wherein said polymeric vehicle is based on silicon, polyurethane, or another biocompatible polymer.

9. Pharmaceutical composition according to claim 6, wherein the carrier is based on a degradable system.

10. Pharmaceutical composition according to claim 9, wherein said degradable carrier is based on chitosan, collagen or another biodegradable carrier.

11. Pharmaceutical composition according to claim 6, wherein the controlled release delivery system is adapted for subdermal implantation.

12. Pharmaceutical composition according to claim 6, wherein the controlled release delivery system is adapted for site specific implantation.

13. A method for the treatment of osteoporosis hypercalcemia of malignancy; heterotopic ossification Paget's disease; or hyperphosphatemia comprising administration of a pharmaceutical composition as defined by claim 5.

14. A pharmaceutical composition comprising an effective amount of a compound according to claim 3 and a pharmaceutically acceptable excipient or carrier.

15. A method for treating irregularities in calcium metabolism or the symptoms associated therewith comprising administering to a host an effective amount of a compound according to claim 3.

16. Bisphosphonate compounds of the formula

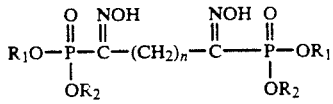

wherein
n = an integer from 3 to 24
$R_1$ = a lower alkyl group, and
$R_2$ = hydrogen or a monovalent alkali metal cation.

17. A compound according to claim 16 having the formula

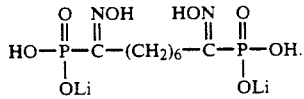

18. The compound according to claim 16 having the formula

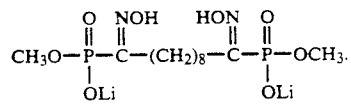

19. A pharmaceutical composition comprising an effective amount of a compound according to claim 16 and a pharmaceutically acceptable excipient or carrier.

20. A method for treating irregularities in calcium metabolism or the symptoms associated therewith comprising administering to a host an effective amount of a compound according to claim 16.

* * * * *

UNITED STATES PATENT AND TRADEMARK OFFICE
CERTIFICATE OF CORRECTION

PATENT NO. : 5,196,409
DATED     : March 23, 1993
INVENTOR(S) : Eli BREUER ET AL It is certified that error appears in the above-identified patent and that said Letters Patent is hereby corrected as shown below:

Col. 9, claim 5, line 19, change "claim 3" to --claim 1--

Col. 10, claim 15, line 9, change "claim 3" to --claim 1--

Col. 10, claim 14, line 4, change "claim 3" to --claim 1--

Signed and Sealed this

Third Day of May, 1994

Attest:

BRUCE LEHMAN

Attesting Officer        Commissioner of Patents and Trademarks